(12) United States Patent
Feldman et al.

(10) Patent No.: US 7,674,436 B1
(45) Date of Patent: Mar. 9, 2010

(54) PORTABLE INDOOR AIR PURIFICATION SYSTEM

(76) Inventors: Vladimir Feldman, 2611 E. 13th St., #5G, Brooklyn, NY (US) 11235; Eduard Iskov, 2440 E. 29th St., #4L, Brooklyn, NY (US) 11235

( * ) Notice: Subject to any disclaimer, the term of this patent is extended or adjusted under 35 U.S.C. 154(b) by 0 days.

(21) Appl. No.: 12/154,703

(22) Filed: May 27, 2008

(51) Int. Cl.
*A61L 9/20* (2006.01)

(52) U.S. Cl. .......... 422/121; 422/24; 422/120; 422/186.3; 96/224; 55/482; 250/432 R

(58) Field of Classification Search ............ 422/24, 422/120–122, 186, 186.3; 96/224; 55/482; 250/432 R, 436
See application file for complete search history.

(56) References Cited

U.S. PATENT DOCUMENTS 5,833,740 A * 11/1998 Brais .......................... 96/16
6,221,314 B1 * 4/2001 Bigelow ...................... 422/24
7,063,820 B2 * 6/2006 Goswami ................. 422/186.3

* cited by examiner

*Primary Examiner*—Sean E Conley
(74) *Attorney, Agent, or Firm*—Law Offices of J. D. Geraigery; Janine D. Geraigery

(57) ABSTRACT

An indoor air purification system and method of same includes a case which removably attaches to an exhaust of cleaning equipment. An air purification chamber housed within the case includes an intake and exhaust wall and side walls, including a first side wall having an outside and inside surface. The intake and exhaust walls of the chamber are covered by aluminum metal mesh filters with a titanium dioxide coating. An ultraviolet-A blacklight blue is mounted to the inside surface of the first side wall of the chamber and includes an elongated u-shaped lamp for activating the titanium dioxide coating. An ultraviolet-C germicidal light for ultraviolet germicidal irradiation is mounted above the ultraviolet-A blacklight blue within the chamber and includes an elongated u-shaped lamp. A solid state high frequency electronic ballast powers and activates the lamps and converts voltage.

15 Claims, 3 Drawing Sheets

PORTABLE INDOOR AIR PURIFICATION SYSTEM

BACKGROUND OF THE INVENTION

Field of the Invention

The invention relates to air purifiers, and more particularly, to a portable indoor air purification system that serves as an attachment to vacuum cleaners, steam cleaners, hot water extractors, and stand-alone air purifiers in order to destroy microorganisms, remove harmful particulates, and eliminate odors from the air through a combination of ultraviolet light and titanium dioxide technology.

Indoor air quality can be affected by various pollutants, including unwelcome microorganisms, harmful particulates and irritating odors. The airborne contaminants emitted from vacuum cleaners, steam cleaners, hot water extraction machines, and air purifiers may only exacerbate the level of impurities contained in the air. By releasing irritating fumes and microorganisms into the air, allergies or other pre-existing conditions may become inflamed, or other respiratory conditions may develop.

The ultraviolet light treatment of such impurities is proven to be especially effective in eliminating a vast array of irritants contained in the air. Ultraviolet germicidal irradiation, commonly used for medical sanitation and sterile work facilities, produces a purifying plasma of purifying hydroxyls that is highly effective at destroying a wide range of microorganisms such as bacteria, viruses, and molds. In combination with titanium dioxide technology, ultraviolet light ignites a photocatalytic oxidation process that helps eliminate odors. Ultraviolet light may also be used to produce safe levels of ozone, which help to oxidize pollutants, and negative ions, which attach to solid particles such as dust pollen and smoke and remove them from the air.

Currently, various air purifiers incorporating one of these technologies are offered in the market to combat indoor air pollutants in select rooms of a home or office. However, a purifier consisting of ultraviolet germicidal irradiation, titanium dioxide, or ozone alone is not as effective at removing contaminants in the air as a purifier containing a combination of those methods. In addition, current air purifiers fail to directly regulate or purify the irritating amount of contaminates which can be released into the air by vacuum cleaners, steam cleaners, hot water extraction machines, and air purifiers. The current invention seeks to eliminate that dilemma by providing a portable air purifier that attaches to the various types of equipment and incorporates ultraviolet light and titanium dioxide technologies in order to purify the air, destroy fumes and odor, and provide significant noise reduction of the equipment it is attached to.

SUMMARY OF THE INVENTION

It is an object of the invention to provide a method of using ultraviolet light technology to improve indoor air quality by significantly reducing the amount of harmful microorganisms, particulates, fumes and odors contained in the air. Accordingly, the invention is an indoor air purification system that uses ultraviolet germicidal irradiation, titanium oxide coating and ultraviolet light lamps.

It is another object of the invention to provide an air purification system that kills bacteria, viruses, mold, mildew and fungi.

It is another object of the invention to provide an air purification system that destroys and neutralizes toxic gases, mycotoxins, spores, chemical fumes, and allergens.

It is another object of the invention to provide an air purification system that removes harmful particulates, dust and mites, cigarette smoke, pet odors and pet dander. Accordingly, the invention removes smaller particles than high efficiency particulate air (HEPA) filters, down to 0.001 microns.

It is another object of the invention to provide an air purification system that uses safe and effective ultraviolet technology in purifying the air.

It is another object of the invention to provide a removable, interchangeable attachment to vacuum cleaners, steam cleaners, hot water extractors and/or stand-alone air purifiers that can be easily mounted onto and removed from the exhaust thereof.

It is yet another object of the invention to provide an air purification system that significantly reduces the motor noise of the equipment it is attached to. Accordingly, the system of the present invention has aluminum mesh filters for reducing motor noise.

It is yet another object of the invention to reduce the level of contaminants emitted from vacuum cleaners, steam cleaners, hot water extractors and/or air purifiers that might aggravate allergies or respiratory conditions.

It is yet another object of the invention to provide a lightweight and portable air purifier system that is also easy to clean and disinfect. Accordingly, there are no filters to change or plates to clean.

It is yet another object of the invention to provide a convenient and aesthetically pleasing air purifier that may complement any home, office, business, school or hospital.

This invention is a portable indoor air purification system and method of same that includes a case which removably attaches to an exhaust of cleaning equipment. An air purification chamber housed within the case includes an intake and exhaust wall and side walls, including a first side wall having an outside and inside surface. The intake and exhaust walls of the chamber are covered by aluminum metal mesh filters with a titanium dioxide coating. An ultraviolet-A blacklight blue is mounted to the inside surface of the first side wall of the chamber and includes an elongated u-shaped lamp for activating the titanium dioxide coating. An ultraviolet-C germicidal light for ultraviolet germicidal irradiation is mounted above the ultraviolet-A blacklight blue within the chamber and includes an elongated u-shaped lamp. A solid state high frequency electronic ballast powers and activates the lamps and converts voltage.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
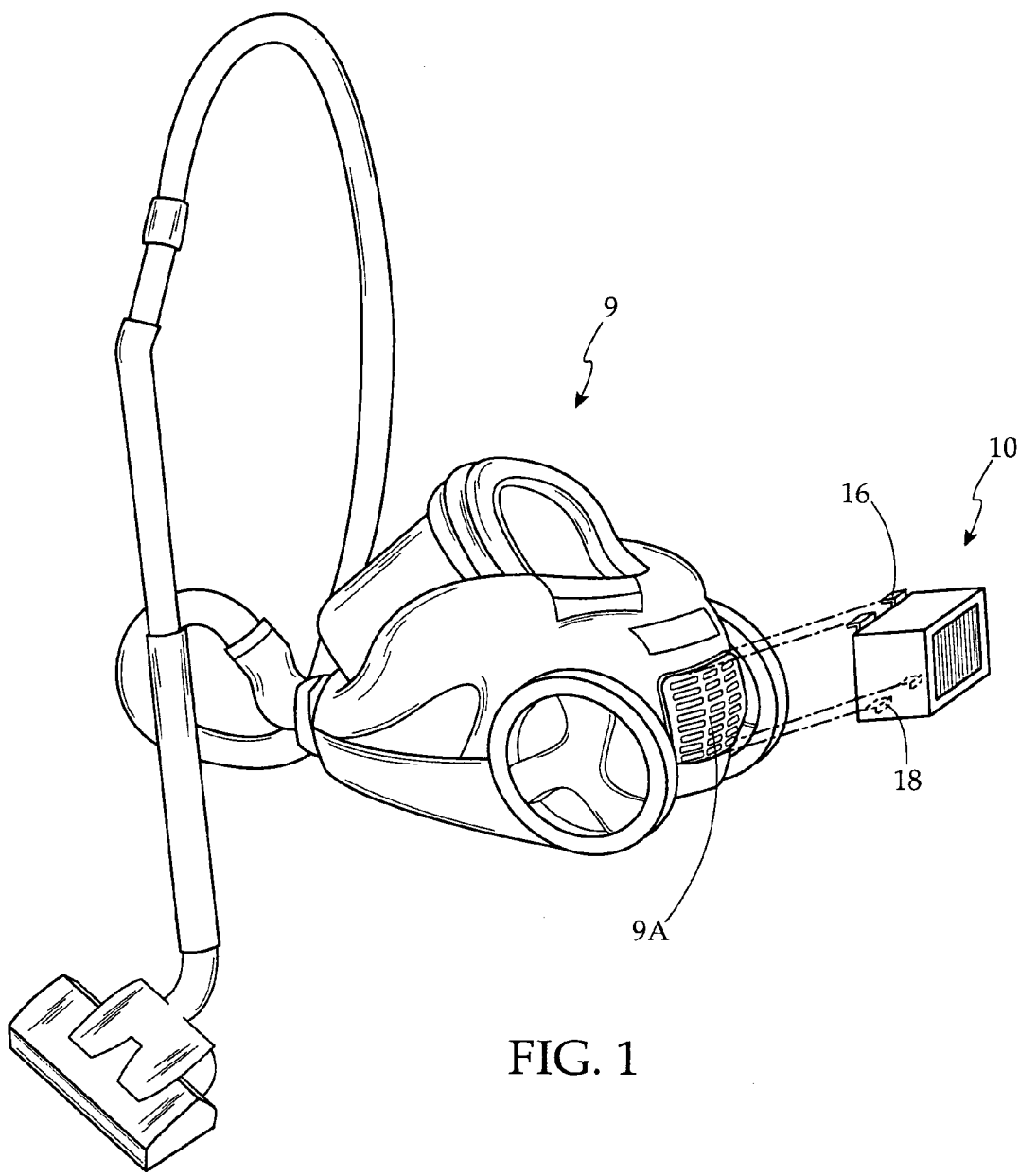
FIG. 1 is a diagrammatic perspective view of the portable indoor air purification system of the present invention in use mounted on an exhaust grill of a vacuum cleaner.

FIG. 1 illustrates an indoor air purification system 10 of the present invention for cleaning and purifying the exhaust air from of a variety of cleaning equipment including a vacuum cleaner, steam cleaner, or hot water extraction machine. The air purification system 10 is a removable and interchangeable attachment that has the capability kill harmful microorganisms and airborne contaminants discarded from an exhaust. For example, here, the air purification system 10 is removably secured by attaching over an exhaust grill 9A of a standard vacuum cleaner 9.

Figure 2:
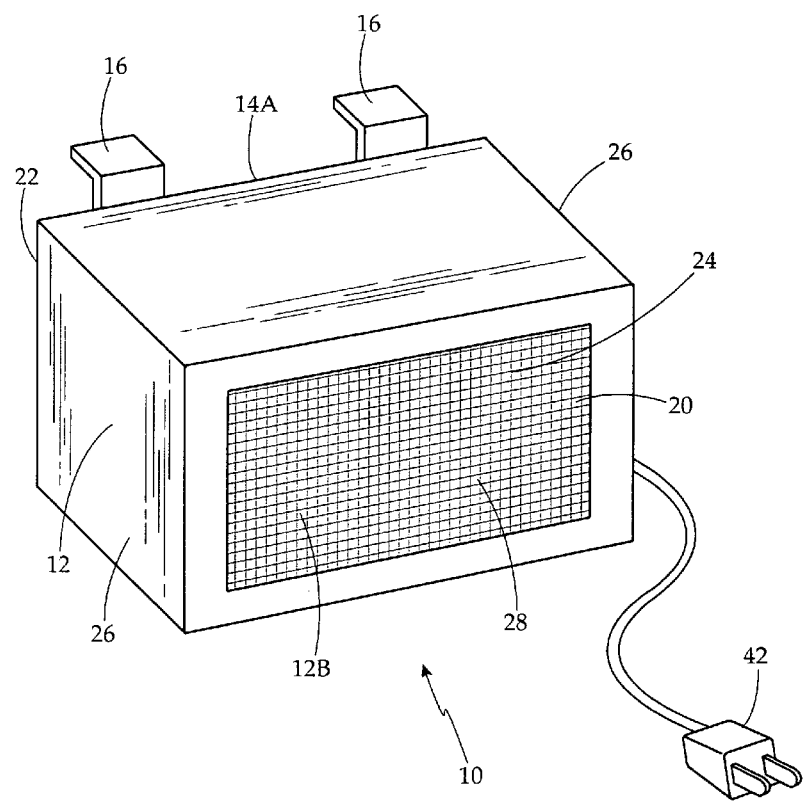
FIG. 2 is a diagrammatic perspective view of the portable indoor air purification system of the present invention having a plastic case having mounting hooks and aluminum mesh filters.

FIG. 2 illustrates the indoor air purification system 10 which includes a substantially rectangular plastic case 12. The case 12 houses a substantially rectangular aluminum purification chamber 20 for cleaning and disinfecting air therein. The case 12 further includes a distal top edge 14A and a distal bottom edge 14B. The distal top edge 14A has at least one, preferably a pair of, substantially square mounting hooks 16, spaced evening apart extending perpendicularly upward therefrom, while the distal bottom edge 14B has a substantially rectangular locking clip 18 centrally positioned and extending perpendicularly downwardly and outwardly therefrom. Together the mounting hooks 16 and locking clip 18 connect and attach the case 12 securely against the exhaust grill 9A of cleaning equipment, here the vacuum cleaner 9. This attaching mechanism is compatible for removably securing the system 10 to a variety of different cleaning equipment.

Preferably, the chamber 20 is three inches by four inches by nine inches, but can vary. The chamber 20 is preferably made out of polished aluminum for better reflection of ultraviolet light therein. The chamber 20 channels contaminated air from the exhaust of the cleaning equipment therethrough, and purifies the air therein, before releasing it into the room. The case 12 protects the chamber 20 during this process and allows for easy attachment and cleaning of the chamber 20. The case 12 includes in a partially cutout rear wall 12A and a partially cutout front wall 12B. The air purification chamber 20 includes an intake wall 22 and an exhaust wall 24 and a pair of side walls 26, including a first side wall 27. The intake and exhaust walls 22 and 24 are opposite one another and correspond respectively with the rear wall 12A and front wall 12B of the case 12. The intake and exhaust walls 22 and 24 of the chamber 20 are substantially covered by aluminum metal mesh filters 28. The aluminum metal mesh filters 28 are integrally coupled against the intake and exhaust walls 22 and 24 and the rear wall 12A and front wall 12B of the case 12, respectively.

Figure 4:
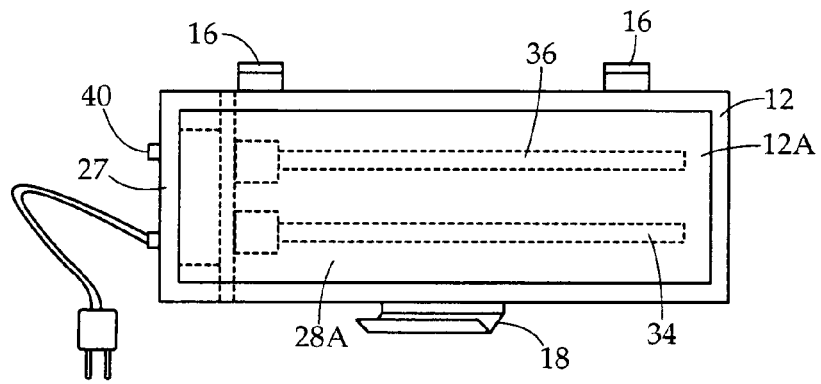
FIG. 4 is a rear elevational view of the air purification chamber of the portable indoor air purification system including the solid state high frequency electronic ballast, ultraviolet-A blacklight blue and ultraviolet-C germicidal light.
Figure 5:
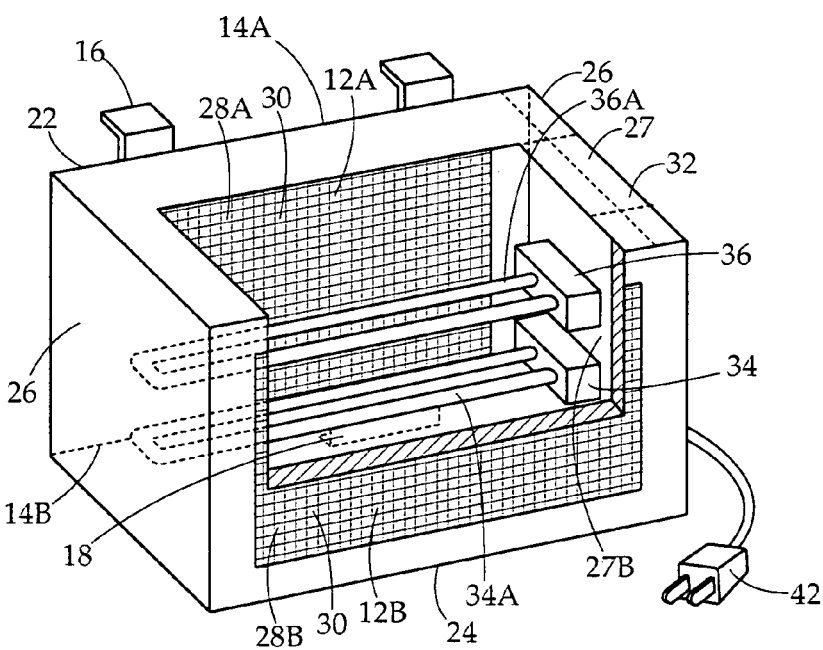
FIG. 5 is an exploded diagrammatic perspective view of the portable indoor air purification system of the present invention, having a partially cutout section for viewing the air purification chamber, aluminum mesh filters, ultraviolet-A blacklight blue, and ultraviolet-C germicidal light.

As shown in FIGS. 4 and 5, the first aluminum mesh filter 28A covering the intake wall 22 allows contaminated air to flow therethrough an into the chamber 20. After purification occurs within the chamber 20, purified air flows out through the opposite second aluminum mesh filter 28B covering the exhaust wall 24. The aluminum mesh filters 28 further provide for significant motor noise reduction from attached complementary equipment. The first and second aluminum mesh filters 28A and 28B include a titanium dioxide (TiO2) coating 30 for activating a TiO2 photo-catalytic oxidation process which exhibits self cleaning and disinfecting properties when exposed to UV radiation. Preferably the titanium dioxide (TiO2) coating 30 includes a primer and a top coat. Free radicals produced by TiO2 oxidize volatile organic compounds which significantly reduces concentration of airborne pollution and odors within the chamber 20.

Figure 3:
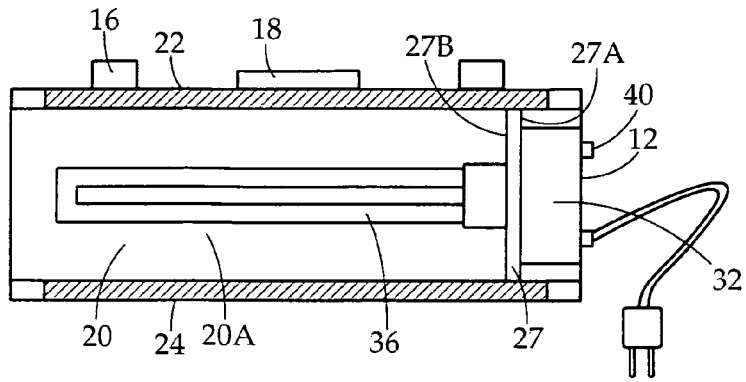
FIG. 3 is a top plan view of the portable indoor air purification system having a chamber including a solid state high frequency electronic ballast and an ultraviolet-C germicidal light.

FIG. 3 illustrates the first side wall 27 of the air purification chamber 20 including an outside surface 27A and an inside surface 27B. A solid state high frequency electronic ballast 32 is positionable between the outside surface 27A of this first side wall 27 of the chamber 20 and the case 12.

FIGS. 4 and 5 illustrate the system 10 of the present invention which utilizes ultraviolet (UV) light. Specifically, ultraviolet light is electromagnetic radiation with wavelengths shorter than visible light and in the present invention is separated into various ranges, including long range UV (UVA) considered "blacklight blue" and short range UV (UVC) considered "germicidal UV". This is preferable for the present invention because at certain wavelengths UV is mutagenic to bacteria, viruses and other micro-organisms.

An ultraviolet-A (UVA) blacklight blue 34 is mounted to the inside surface 27B of the first side wall 27 of the chamber 20. The UVA blacklight blue 34 includes a lamp 34A which is elongated and u-shaped and extends outwardly perpendicular to the first side wall 27 and into the center 20A of the chamber 20.

The UVA blacklight blue 34 is more commonly referred to as a UV light, black light, Wood's light, and is preferably a lamp that emits long wave UV radiation and very little visible light. Typically, fluorescent black lights are typically made in the same fashion as normal fluorescent lights except that only one phosphor is used and the normally clear glass envelope of the may be replaced by a deep-bluish-purple glass, a nickel-oxide-doped glass, which blocks almost all visible light above 400 nanometers. The color of such lamps is often referred to in the trade as "blacklight blue" or "BLB."

Typically UVA blacklight blue 34 does produce light in the UV range, but their spectrum is confined to the longwave UVA region. UVA-radiation generates free radicals and causes the indirect DNA damage. The UVA blacklight blue 34 has a direct light spectrum of 368 nanometers (nm) for activating the TiO2 photo-catalytic oxidation process. TiO2 photo-catalytic oxidation process, namely the titanium dioxide (TiO2) coating 30 on the aluminum mesh filters 28 is activated when exposed to the UVA blacklight blue 34 which acts as a photo-catalyst in removing odors and fumes from air passed through the chamber 20. Thus, neutralizing odors and reducing the concentration of pollutants contained in any air which flows through the chamber 20.

Moreover, the present invention uses ultraviolet germicidal irradiation (UVGI) as a sterilization method that uses ultraviolet light at sufficiently short wavelength to break down micro-organisms. Here, an ultraviolet-C (UVC) germicidal light 36 is mounted to the inside surface 27B of the first side wall 27 of the chamber 20 above the UVA blacklight blue 34. The ultraviolet-C (UVC) germicidal light 36 includes a lamp 36A which is elongated and u-shaped and extends outwardly perpendicular to the first side wall 27 and into the center 20A of the chamber 20.

The UVGI system exposes the chamber 20 to germicidal UV through the lamp 36A. The ultraviolet-C (UVC) germicidal light 36 has a UVC spectrum of 257 nanometers for effectively killing many microorganisms, such as germs, bacteria, viruses, and severe acute respiratory syndrome (SARS) spores. The forced flow of air through the chamber 20 ensures exposure.

The solid state high frequency electronic ballast 32 powers and activates both lamps 34A and 36A simultaneously to ensure proper starting, while automatically converting voltage of said lamps 34A and 36A from 110 volts to 220 volts.

The system 10 is powered by a power switch 40 coupled to the case 12 and one of the side walls 26 of the chamber 20. A power cord 42 connects the power switch 40 to a standard power outlet. In additional embodiment, batteries, or alternative sources for powering the system 10 are contemplated.

In use, the system 10 enables a method for destroying microorganisms, removing harmful particulates, and eliminating odors. The system 10 is attachable to an exhaust of a vacuum cleaner 9 or other like cleaning apparatus (as shown in FIG. 1). The first aluminum mesh filter 28A covering the intake wall 22 allows contaminated air to flow from the exhaust grill 9A of the vacuum cleaner 9 therethrough an into the chamber 20. While in the chamber 20 the TiO2 coating 30 removes odors and fumes from the air. The UVA blacklight blue 34 activates the TiO2 photo-catalytic oxidation process, while the UVC germicidal light 36 kills harmful bacteria and viruses. After purification occurs within the chamber 20, purified air is exhausted or flows out through the opposite second aluminum mesh filter 28B covering the exhaust wall 24.

In conclusion, herein is presented an indoor air purification system 10. The invention is illustrated by example in the drawing figures, and throughout the written description. It should be understood that numerous variations are possible, while adhering to the inventive concept. Such variations are contemplated as being a part of the present invention.

What is claimed is:

1. An indoor air purification system for cleaning and purifying exhaust air, comprising:
    a substantially rectangular plastic case housing a substantially rectangular aluminum purification chamber for cleaning and disinfecting air therein, said case including a distal top edge and a distal bottom edge, said distal top edge having a pair of substantially square mounting hooks spaced evening apart extending perpendicularly upward therefrom, said distal bottom edge having a substantially rectangular locking clip centrally positioned and extending perpendicularly downwardly and outwardly therefrom, said case including a partially cutout rear wall and a partially cutout front wall, said chamber including an intake wall and an exhaust wall and a pair of side walls, including a first side wall having an outside surface and an inside surface, said intake and exhaust walls of said chamber positionable opposite one another and corresponding respectively with said rear wall and front wall of said case, said intake and exhaust walls of said chamber are substantially covered by aluminum metal mesh filters, including a first and second aluminum metal mesh filters, said first aluminum metal mesh filter integrally coupled against said intake wall of said chamber and said second aluminum metal mesh filter integrally coupled against said exhaust walls of said chamber, said first and second aluminum mesh filters including a titanium dioxide coating for activating a titanium dioxide photo-catalytic oxidation process producing free radicals by said titanium dioxide that oxidize volatile organic compounds;
    an ultraviolet-A blacklight blue is mounted to said inside surface of said first side wall of said chamber, said ultraviolet-A blacklight blue includes an elongated u-shaped lamp which extends outwardly perpendicular to said first side wall and into a center of said chamber;
    an ultraviolet-C germicidal light for ultraviolet germicidal irradiation is mounted to said inside surface of said first side wall of said chamber above said ultraviolet-A blacklight blue, said ultraviolet-C germicidal light includes an elongated and u-shaped lamp which extends outwardly perpendicular to said first side wall and into a center of said chamber;
    an electronic ballast positionable between said outside surface of said first side wall of said chamber and said case, said electronic ballast includes solid state electronic circuitry including a printed circuit board and powers and activates said lamps of said ultraviolet-A blacklight blue and said lamp of said is said ultraviolet-C germicidal light simultaneously, while automatically converting voltage of said lamps from 110 volts to 220 volts;
    a power switch coupled to said case and one of said side walls of said chamber; and
    a power cord connecting said power switch to a standard power outlet.

2. The indoor air purification system of claim 1, wherein the case is detachable, removable and interchangeable.

3. The indoor air purification system of claim 1, wherein the chamber is made out of polished aluminum.

4. The indoor air purification system of claim 1, wherein the ultraviolet-A blacklight blue has a direct light spectrum of 368 nanometers for activating the titanium dioxide photo-catalytic oxidation process.

5. The indoor air purification system of claim 1, wherein the ultraviolet-C germicidal light has a UVC spectrum of 257 nanometers for effectively killing many microorganisms, such as germs, bacteria, viruses, and severe acute respiratory syndrome spores.

6. An indoor air purification system within a case which removably attaches to exhaust of cleaning equipment for cleaning and purifying exhaust air, comprising:
    a substantially rectangular aluminum purification chamber for cleaning and disinfecting air therein, said chamber including an intake wall and an exhaust wall and a pair of side walls, including a first side wall having an outside surface and an inside surface, said intake and exhaust walls of said chamber positionable opposite one another, said intake and exhaust walls of said chamber are substantially covered by aluminum metal mesh filters, including a first and second aluminum metal mesh filters, said first aluminum metal mesh filter integrally coupled against said intake wall of said chamber and said second aluminum metal mesh filter integrally coupled against said exhaust walls of said chamber, said first and second aluminum mesh filters including a titanium dioxide coating for activating a titanium dioxide photo-catalytic oxidation process producing free radicals by said titanium dioxide that oxidize volatile organic compounds;
    an ultraviolet-A blacklight blue is mounted to said inside surface of said first side wall of said chamber, said ultraviolet-A blacklight blue includes an elongated u-shaped lamp which extends outwardly perpendicular to said first side wall and into a center of said chamber;
    an ultraviolet-C germicidal light for ultraviolet germicidal irradiation is mounted to said inside surface of said first side wall of said chamber above said ultraviolet-A blacklight blue, said ultraviolet-C germicidal light includes an elongated and u-shaped lamp which extends outwardly perpendicular to said first side wall and into a center of said chamber; and a solid state high frequency electronic ballast positionable between said outside surface of said first side wall of said chamber and said case, said electronic ballast powers and activates said lamps of said ultraviolet-A blacklight blue and said lamp of said is said ultraviolet-C germicidal light simultaneously, while automatically converting voltage of said lamps from 110 volts to 220 volts.

7. The indoor air purification system of claim 6, wherein the case is substantially rectangular and plastic and includes a distal top edge having a pair of substantially square mounting hooks spaced evening apart extending perpendicularly upward therefrom, and a distal bottom edge having a substantially rectangular locking clip centrally positioned and extending perpendicularly downwardly and outwardly therefrom.

8. The indoor air purification system of claim 7, wherein the case includes a partially cutout rear wall and a partially cutout front wall, and the intake and exhaust walls of said chamber corresponding respectively with said rear wall and front wall of said case.

9. The indoor air purification system of claim 7, further comprising a power switch coupled to said case and one of said side walls of said chamber.

10. The indoor air purification system of claim 9, further comprising a power cord connecting said power switch to a standard power outlet.

11. The indoor air purification system of claim 6, wherein the case is detachable, removable and interchangeable.

12. The indoor air purification system of claim 6, wherein the chamber is made out of polished aluminum.

13. The indoor air purification system of claim 6, wherein the titanium dioxide coating includes a primer and a top coat.

14. The indoor air purification system of claim 6, wherein the ultraviolet-A blacklight blue has a direct light spectrum of 368 nanometers for activating the titanium dioxide photocatalytic oxidation process.

15. The indoor air purification system of claim 6, wherein the ultraviolet-C germicidal light has a UVC spectrum of 257 nanometers for effectively killing many microorganisms, such as germs, bacteria, viruses, and severe acute respiratory syndrome spores.

* * * * *